United States Patent [19]

Liss et al.

[11] Patent Number: 4,784,142
[45] Date of Patent: * Nov. 15, 1988

[54] METHODOLOGY FOR ELECTRONIC DENTAL ANALGESIA

[75] Inventors: Saul Liss; Bernard Liss, both of Glen Rock; Samuel Krakower, Teaneck, all of N.J.

[73] Assignee: Pain Suppression Labs, Inc., Wayne, N.J.

[*] Notice: The portion of the term of this patent subsequent to Nov. 5, 2002 has been disclaimed.

[21] Appl. No.: 926,971

[22] Filed: Nov. 4, 1986

Related U.S. Application Data

[63] Continuation-in-part of Ser. No. 868,652, May 30, 1986, Ser. No. 860,745, May 7, 1986, and Ser. No. 640,104, Aug. 13, 1984, Pat. No. 4,627,438, which is a continuation-in-part of Ser. No. 569,476, Jan. 9, 1984, Pat. No. 4,550,733, said Ser. No. 868,652, is a continuation-in-part of Ser. No. 618,144, Jun. 1, 1984, Pat. No. 4,614,193, Ser. No. 640,104, , and Ser. No. 860,745, , which is a continuation-in-part of Ser. No. 618,144, , and Ser. No. 640,104, , said Ser. No. 618,144, and Ser. No. 640,104, each is a continuation-in-part of Ser. No. 569,476.

[51] Int. Cl.$^4$ .................................................. A61N 1/34
[52] U.S. Cl. .................................. 128/421; 128/419 R
[58] Field of Search .................... 128/419 R, 421, 422, 128/423

[56] References Cited

U.S. PATENT DOCUMENTS

| | | | |
|---|---|---|---|
| 3,640,284 | 2/1972 | De Langis | 128/422 |
| 3,791,373 | 2/1974 | Winkler et al. | 128/422 |
| 4,155,366 | 5/1979 | Di Mucci | 128/421 |
| 4,503,863 | 3/1985 | Katims | 128/421 |

Primary Examiner—Ruth S. Smith
Attorney, Agent, or Firm—Hopgood, Calimafde, Kalil, Blaustein & Judlowe

[57] ABSTRACT

Dental electronic analgesia apparatus and methodology employs a transutaneous electronic wave to suppress perceived pain during trauma associated with dental procedures. During a pre-treatment phase, a first electrode is placed over the right temporal area of the patient's head and a second electrode on the left temporal area of a patient's head. In addition, during the operative phase, an additional electrode is placed on the buccal side of the gum adjacent the work area, and optional additional electrodes are disposed on the web of the ipsalateral hand and/or on the web of the contralateral hand. An electronic current wave comprising relatively high frequency pulses with a low frequency amplitude modulation is then applied between the first to the second electrodes. The apparatus of the instant invention has been found to block pain in most subjects with a low level current without any chemical intervention, or with a reduced dosage of local anesthesia.

20 Claims, 6 Drawing Sheets

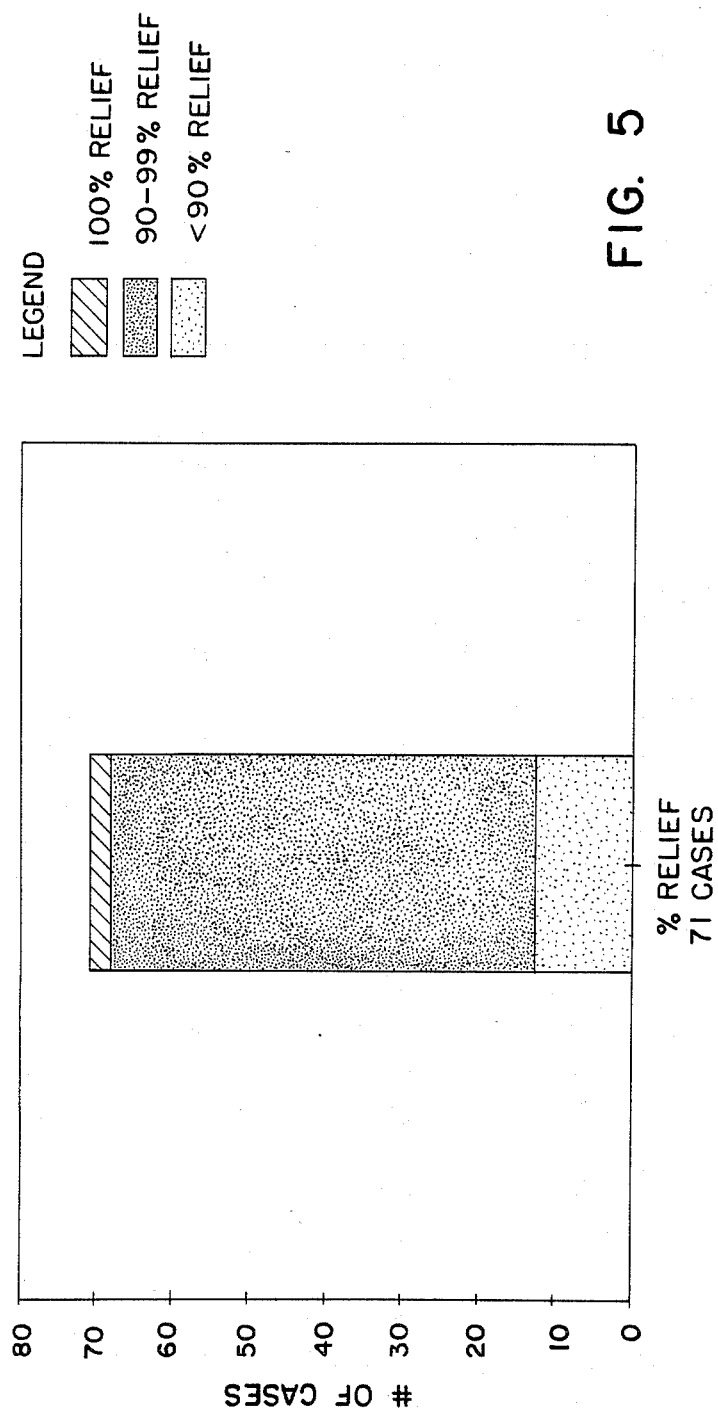

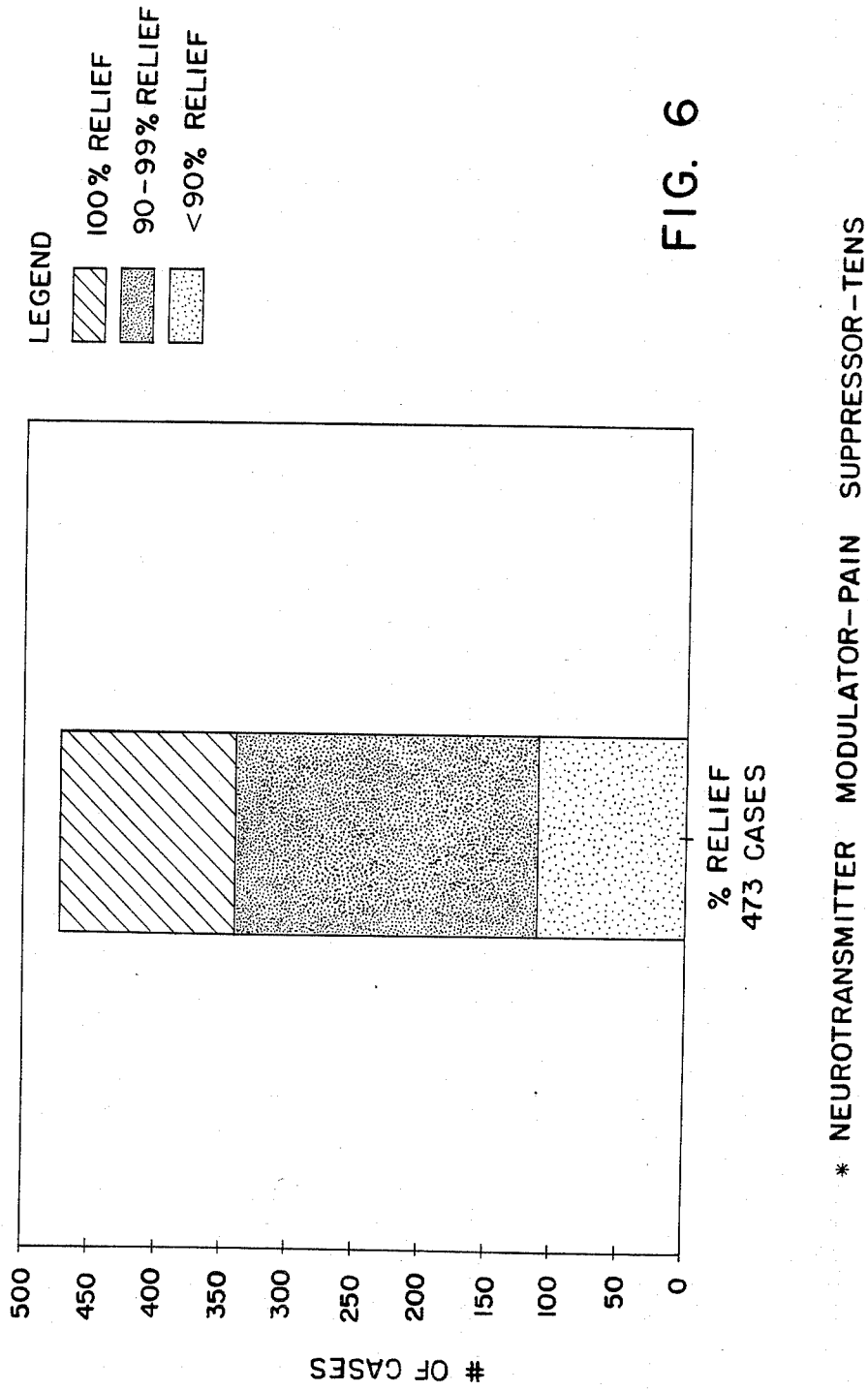

METHODOLOGY FOR ELECTRONIC DENTAL ANALGESIA

This application is a continuation-in-part of the following applications: (1) Ser. No. 640,104 filed on Aug. 13, 1984, now U.S. Pat. No. 4,627,438 which is a continuation-in-part of Ser. No. 569,476, filed on 1-9-84 now U.S. Pat. No. 4,550,733; (2) Ser. No. 860,745 filed on May 7, 1986 which is a continuation-in-part of Ser. No. 618,144 filed on 6-1-4, now U.S. Pat. No. 4,614,193 and Ser. No. 640,104, now U.S. Pat. No. 4,627,438, both of which U.S. Pat. Nos. 4,614,193 and 4,627,438 are continuations-in-part of Ser. No. 569,476, now U.S. Pat. No. 4,550,733; and (3) Ser. No. 868,652 filed on May 30, 1986 which is a continuation-in-part of (a) Ser. No. 618,144, now U.S. Pat. No. 4,614,193, (b) Ser. No. 640,104, now U.S. Pat. No. 4,627,438, both of which U.S. Pat. Nos. 4,614,193 and 4,627,438 are continuations-in-part of Ser. No. 569,476, now U.S. Pat. No. 4,550,733; and (c) application (2).

This invention relates to electronic pain suppression apparatus and methodology and, more specifically, to dental analgesia apparatus and procedure for relieving pain during dental procedures.

It is an object of the present invention to provide improved dental analgesic methodology.

More specifically, an object of the present invention is the electronic provision of dental analgesia in a safe, efficient and rapid manner to suppress perceived pain during dental procedures such as scaling, prophylaxis and restorations.

It is a further object of the present invention to provide electronic dental trancutaneous electronic nerve stimulating equipment operative at very low, milliampere current levels, which relieves perceived pain during dental procedures; and which for the most part, is effective without any requirement for chemical local anesthesia.

The above and other objects and features of the instant invention are realized in a specific illustrative dental electronic analgesia apparatus and methodology which employs a transcutaneous electronic wave to suppress perceived pain during trauma associated with dental procedures. A first electrode or electrodes are placed proximate to the oral cavity area and a second electrode or electrodes are placed in an area(s) which is outside of the oral cavity area. More specifically, the electrode(s) proximate to the oral cavity area are placed intraorally.

Preferably, prior to beginning the dental procedure (pre-treatment phase), a pair of electrodes is placed transcranially. A positive contact electrode is placed at one side of the head of the patient, e.g., over one temporal area and a negative contact electrode is placed at the opposite side of the patient's head, e.g., over the opposite temporal area. The pair of electrodes can be in the form of a headset. Advantageously, the positive and negative electrodes are respectively placed at the right and left sides of the patient's head, e.g., over the right and left temporal areas. These electrodes induce trancranial stimulation during the pre-treatment phase. They are left in place for approximately ten minutes after the current is adjusted to establish a sub-threshold level. The threshold level is defined as that point at which sensory stimulation is first noticed. This point is recorded and the operating current is then reduced to a subthreshold level. Although transcranial stimulation is typically used alone during the pre-treatment phase and in conjunction with additional electrodes during the operative phase, as will be discussed below, trancranial stimulation alone may be used effectively for some dental procedures.

Typically, for use during dental procedures (operative phase), an additional contact electrode, preferably a positive contact electrode, is placed intraorally, e.g., on the buccal side of the patient's gum, adjacent to the tooth or teeth to be subjected to the procedure. This electrode can be contained within a conventional cotton roll or via some other electrical conducting means. For some dental procedures, the operative procedure can take place with the stimulation provided by the transcranially placed electrodes in conjunction with the buccal electrode.

Alternatively, an additional contact electrode, preferably a negative contact electrode, can be placed on the web of the ipsalateral (same side) hand or on the web of the contralateral (opposite side) hand as the tooth or teeth being worked on, or on the webs of both hands.

The transcranial electrode on one side of the head, preferably the right side, along with the buccal electrode, are designated as the first electrodes, creating a first potential. The transcranial electrode on the opposite side of the head along with the optional electrodes on the webs on either or both of the ipsalateral and contralateral hands are designated as the second electrodes, creating a second potential.

An electronic current wave comprising relatively high frequency pulses with a low frequency modulation is then applied from the first to the second electrodes.

The apparatus of the instant invention has been found to block pain in most subjects with a relatively low level current without the necessity of chemical intervention, or with a reduced dosage of local anesthesia.

The above and other features and advantages of the instant invention will become more clear from the following detailed description of a specific illustrative embodiment thereof, presented hereinbelow in conjunction with the accompanying drawings in which:

FIG. 5 is a graph showing the percent of relief in scaling and prophylaxis, using the method of the invention; and FIG. 6 is a graph showing the percent of relief in restorative procedures, using the method of the invention;

Figure 1:
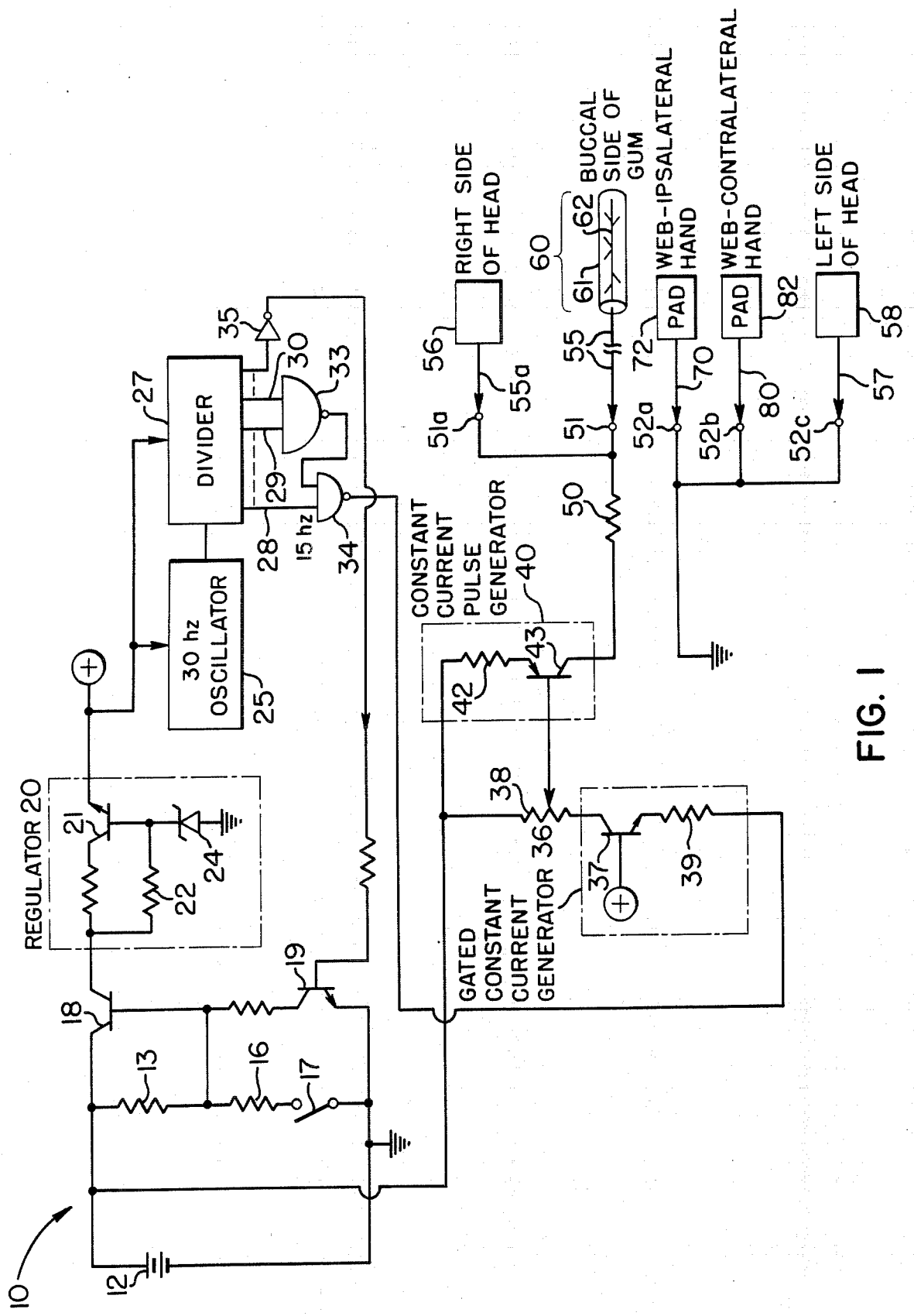
FIG. 1 is a schematic diagram of electronic dental anesthesia apparatus embodying the principles of the present invention.

To illustrate performance of the instant invention in overview, the apparatus of FIG. 1 is utilized to block pain perceived by a patient who is subjected to a trauma producing (e.g., invasive) dental procedure. During the pretreatment phase, a contact electrode 56 (FIG. 1) is placed on the right side of the head, e.g., over the right temporal area and a contact electrode 58 is placed on the left side of the head, e.g., over the left temporal area. During the operative phase, an additional electrode 60 is placed on the buccal side of the patient's gum adjacent to the tooth or teeth being subjected to the procedure. Depending on the particular dental procedure being performed, additional electrode 72 and/or 82 are respectively placed on the web of the ipsalateral hand, i.e., the hand on the side of the body which is the same as the tooth or teeth being worked upon, and/or on the web of the contralateral hand, i.e., the hand on the opposite side of the body, as the tooth or teeth being worked upon. An electronic wave (depicted in FIG. 2D) is then applied between the first electrodes 56 and 60 which are connected in common, and the second electrodes 58, 72 and 82 which are connected in common. The wave form of FIG. 2D comprises a low level (maximum of 4 milliamperes) pulse train of relatively high frequency, e.g., between 12 and 20 khz modulated in amplitude by a relatively low frequency wave in the range of 8 to 20 hz. The low frequency wave is preferably non-symmetrical (that shown in FIG. 2D), for example, characterized by a 3:1 duty cycle, being on three quarters of the time and off one quarter of the recurring period. For concreteness only and without limitation, it will hereinafter be assumed that the high frequency pulse occurs at a 15 khz rate and 1-4 m.a. level, during the pretreatment phase and 1 to 4 m.a. level during the operative phase, while being subject to a 15 hz modulation with a 3:1 duty factor.

Figure 2:
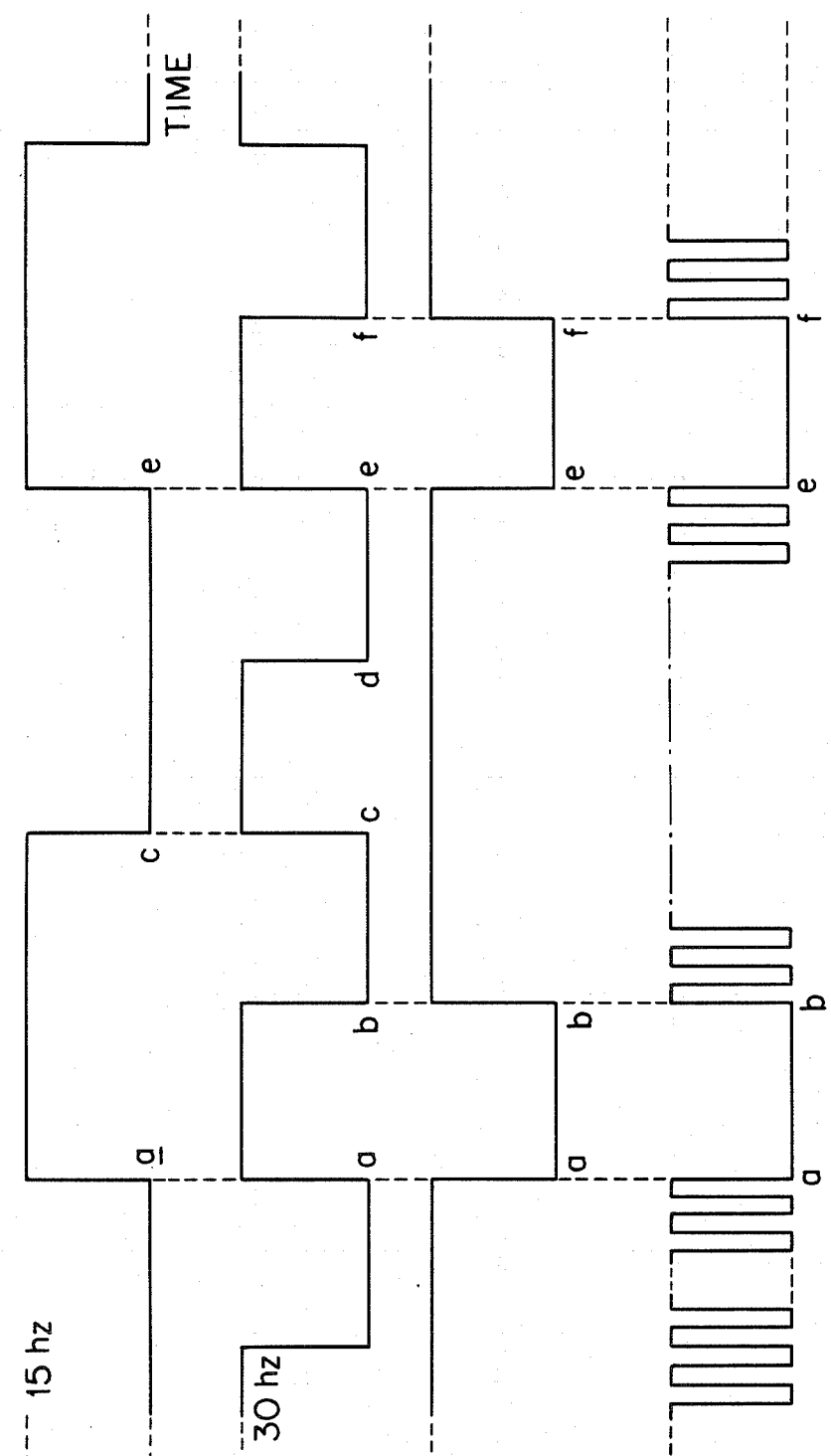
FIG. 2A through 2D are wave forms illustrating the operation of the FIG. 1 apparatus.

We have found that the wave of FIG. 2D is effective in the majority of patients to block the pain perceived during dental procedures. In a fraction of that minority requiring additional chemical intervention, the local anesthesia required is reduced.

The particular mechanism causing elimination of the perceived dental pain is believed to follow from the increase in serotonin produced by the body responsive to the low frequency modulation envelope introduced into the body, with the high frequency wave constituent serving as a transcutaneous carrier for the low frequency modulation.

Various theories have been proposed to characterize the mechanism of perceived pain, and of the manner in which such pain is obviated. The following are presented for possible edification, and without limitation, as to the instant invention. Beginning with a discussion of a purely anatomical explanation, the autonomic nervous system is governed by two antagonistic systems: the sympathetic and the parasympathetic. The first is mediated by nerves which release norepinephrine and the second by those which release serotonin. The neurotransmitter serotonin is thought to be associated with behavioral sedation and sleep, increased para-sympathetic output in the periphery, decreased locomotor activity and reduced responsiveness to external stimulation. An increase in brain serotonergic neurotransmission can lead to the reversal of biological arousal, and therefore suppression of the sensation of pain. The disclosure of Rita B. Messing, "Behavioral Effects of Serotonin Neurotoxins" *Annals, N.Y. Acad. Sci.*, 1978: 480–496, is hereby incorporated by reference. Electronic stimulation of tissue has been shown to increase the brain serotonergic neurotransmission and thus produce analgesia.

Another explanation of the analgesic effects of the presently claimed invention depends on the interference with the neural signal's path. The first order neuron in the pathway for pain and temperature synapses as it enters the spinal cord with a neuron in the dorsal column of gray matter. The axon of this second-order neuron crosses the gray matter to the opposite side of the spinal cord, where it courses upward as a component of the lateral spinothalamic tract. Passing to the thalamus the fiber synapses in a nucleus in this region with a third-order neuron, which relays the impulse to the sensory area of the cerebral cortex. Upon arrival of the impulse to the fifth cranial nerve, pain from the face and head is consciously perceived.

The use of electroanalgesia to block pain may be explained by the "spinal gating" hypothesis. Stimulation of afferent inhibitory neurons, would "close the spinal gate" to prevent pain impulses from being propagated from the spinal cord to the brain. The gate mechanism may be embedded in the cells of the substantia gelatinosa. The mechanism would both sum up the net stimulus due to excitatory and inhibitory signals converging on the spinal cord from afferent fibers, and then transmit the net signal to brain centers. (There may be a second gate, blocking signals that bypass the first gate, higher up in the central nervous system, either in the brainstem or the central medianum of the thalamus.) Second, it would coordinate both pain and its interpretation so that either the pain impulses themselves would not reach the brain centers, or the coordination brought about by the gating system would alter the interpretation and pain would not be perceived.

A third theory of pain suppression depends on the nociceptive system, defined as an ancestral multi integrated apparatus which includes pain sensation. Pain is produced by excitation of functionally distinct types of nociceptors which have yet to be entirely defined anatomically. According to Becker, "The Basic Biological Data Transmission and Control System Influenced by Electrical Forces" *Annals, N.Y. Acad. of Sci.*, 1972, 236–239, the sophisticated action potential system coexists with this basic primitive analog system. Different types of pain may be related to the activation of different proportions of both systems. According to Melzack and Wall, "Pain Mechanisms, a New Theory", *Science*. 1965, 150: 971–979, large non-nociceptive fibers exert presynaptic inhibitory effects on the endings of small nociceptive fibers in the dorsal horn. Substantia gelatinosa interneurons mediate this inhibition. The large fiber discharge tends to block the transmission of input from the small afferent neurons before it reaches the relay neurons. According to the "gate control theory", electrical currents achieve a quantitative superiority to nociceptive impulse at the "neurologic gates" that transmit pain to higher centers; thus, transmission of painful impulses is blocked. Further, Kerr in "Pain," *Mayo Clin. Proc.*, 1975, 50:685–590, notes that electronic stimulation of large fiber input alleviates pain because of its affect on the central nociceptive pathways. When large fibers are electrically excited, widespread activation of gelatinosa neurons results in inhibitory impulses being delivered to marginal neurons.

Other theories of electroanalgesia include the inducement of neurons to manufacture an endogenous opiate that interacts with pain receptors to produce analgesia similar to that produced by morphine, See, Meyer C. A., Fields J. L.: "Causalgia treated by selective large fibre stimulation of peripheral nerve", *Brain*, 1972; 95: 163–168; and the effect on trigeminothalamic A - beta neurons, See, Dubner R: "Neuro physiology of Pain", *Dent. Clin. North Am.*, 1978, 22: 11–30.

While the precise operative mechanism may be the subject of debate, the fact of the dental analgesia produced by the instant invention is not.

As above noted, the composite electrode 60 is inserted in the oral cavity on the buccal side of the gum in the work area vicinity. The electrode is connected via a lead 55 to a connector terminal 51 associated with the electronic apparatus, where the lead terminates in a wire broach area 62 having plural barbs projecting radially outward and canted therefrom. The barbed wire broach 62 is inserted into a cotton swab 61 which is made wet to provide electrical conductivity between the patient's gum and the wire end 62. The barbed projections on wire broach 62 reduce the impedance between the wetted cotton and the metallic conductor 62 by increasing contact surface area while also mechanically retaining the cotton. Electrified cotton rolls can also be fabricated by puncturing a longitudinal hole in a quilted or other type cotton roll, inserting a stripped wire tip therein, and placing a dab of glue to hold the wire into the cotton roll matrix. The electrodes 56, 58, 72 and 82 constitute connection lands or pads to the patient's skin in any of the diverse means per se well known to those skilled in the art.

The FIG. 1 electronic apparatus 10 for generating and applying the wave form of FIG. 2D will now be specifically considered. A battery 12 is connected to a PNP series pass transistor 18 which, in turn, selectively passes the voltage from battery 12 through a voltage regulator 20 to form the positive direct current voltage supply for the apparatus 10 electronics. The unit is first turned on by momentarily closing a power-on switch 17. This applies a low voltage to the base of PNP transistor 18, turning that device on and effectively coupling the potential of battery 12 to a series pass transistor 21 in the voltage regulator 20. Because the final output of a counter or divider chain 27 is initially low on power turn on, the resulting high output of inverter 35 applies a high potential to the base of transistor 19, turning it on and thereby latching PNP transistor 18 to its conductive condition when switch 17 is released. This maintains the electronic apparatus on for a desired period (in excess of the time required to complete the dental procedure) which is determined by the frequency of an oscillator 25 and the division factor of the divider 27, i.e., the period required for the most significant stage of the counter 27 to reach its high or binary "1" state. The switched power supply assures that the electronic apparatus is not inadvertently left on to unduly discharge the battery 12.

The regulated output of battery 12 applied through PNP transistor 18 is converted to a lower regulated value by the regulator 20. Regulator 20 is per se well known and includes the series pass NPN transistor 21 having a constant voltage applied to the base thereof by a Zener diode 24 energized by a resistor 22. The constant potential output of regulator 20, which serves as the supply voltage for much of the remaining electronics of FIG. 1 is the characteristic reverse excitation voltage of Zenor diode 24 less about 7/10 of a volt for the base-emitter drop of transistor 21.

As above noted, the active power supply interval for circuit 10 of the drawing is fixed and preset to a period which will exceed normal dental procedures. The above-discussed time out circuitry is employed to assure that the unit is not inadvertently left on. Many ways of achieving this result will be readily apparent to those skilled in the art. For example, a variable time out may be provided by employing a switch to connect the input of inverter 35 to varying ones of the more significant stage outputs of the pulse counter chain 27. Further, separate electronic or electromechanical timer apparatus, fixed or variable, all per se well known, may be employed to supply a positive potential to the base of transistor 19 for the desired on period; and to switch off the base drive to transistor 19, thereby turning off series pass transistor 18, when the desired operative period has passed.

A time base oscillator 25 supplies an input to the pulse counter or divider chain 27. The frequency of oscillator 25 is chosen for convenience to be an integral multiple of the pulse frequency (FIG. 2D) desired for delivery to the patient. For the assumed 15 khz desired frequency, a 30 khz oscillation repetition rate may be usefully employed for oscillator 25, such that the 15 khz signal is derived at a divide-by-two tap 28 of divider chain 27. The 15 khz signal is supplied as one input to a NAND gate 34, the output of which corresponds to the ultimately desired wave of FIG. 2D. Outputs 29 and 30 of divider 27 are supplied as inputs to a NAND gate 33, the output of which is supplied as a second input to the NAND gate 34. The output 29 of divider 27 supplies the 30 hz wave of FIG. 2B (pulse division factor 1,000 at tap 29), while the 15 hz wave of FIG. 2A is supplied at a divider output 30 (divider factor 2,000). Logic gate 33 generates the output wave of FIG. 2C, being at its high or Boolean "1" value when either of the waves of FIGS. 2A or 2B is low (i.e., preceding the time a during the interval b-e, and following time f). Correspondingly, during the periods a-b and e-f, when the output at divider 27 taps 29 and 30 are both high, the output of gate 33 is low (Boolean "0" value).

The wave form of FIG. 2C is supplied as one input to the gate 34 together with the 15 khz pulse train at the divide-by-two counter 27 output port 28. Accordingly, the output of NAND gate 34 switches between its high and low state during the periods when the FIG. 2C wave is high, i.e., preceding time a, during the interval b-e, following the time f, and so forth for the recurring pattern illustrated by FIGS. 2A-2D.

The voltage wave form of FIG. 2D is converted to a current in the milliampere range for application to the patient by the following circuitry of FIG. 1. As a first matter, a gated constant current generator 36 passes a gated current (either off or of a fixed value) through a potentiometer 38 under control of the output of the NAND gate 34. When the output of NAND gate is low, a transistor 37 in constant current generator 36 is on and a current substantially given by the positive potential output of regulator 20 (applied to the base of transistor 37) less a 7/10 of a volt base emitter drop for the transistor 37, divided by the resistance value of the resistance 39 in the emitter circuit of transistor 37. The voltage at the variable tap of the potentiometer 38 is supplied to the base of a PNP transistor 43 of a constant current pulse generator 40. The output of pulse generator 40 is a current which switches between its off (zero current) state, and a value given by the voltage at the potentiometer 38 tap, less a diode drop for the emitter-base of transistor 43, divided by the resistance value of resistor 42 connected in the emitter circuit of the PNP device 43. This pulsed current output of pulse generator 40 corresponds in wave form to FIG. 2D, and is at a level, determined by the setting of potentiometer 38, in the low milliampere range. It is this current pulse which is ultimately delivered to the patient to provide the requisite dental analgesia.

In a typical application the patient is provided with the potentiometer 38. The potentiometer is first turned up so that the administered current pulses provide a noticeable tingling sensation in the oral cavity of the patient. The patient is then instructed to turn down the potentiometer adjustment until the sensation just disappears. This will provide the amount of transcutaneous electronic stimulation to suppress the perception of pain otherwise engendered by the dental procedure underway. The potentiometer setting may be adjusted by the patient as required as the dental work progresses.

The current pulses from generator 40 pass through a protective, series limiting resistor 50 to output terminals 51 and 51a connected in common, through respective leads 55 and 55a connected to respective terminals 51 and 51a, to respective barbed wire broach 62 and electrode 56 on the right side of the head. The current pulses pass transcutaneously into the patient at the right side of the head and at the buccal gum station. The current pulses reach the patient's gum through the wetted cotton 61 surrounding wire broach 62 disposed on the buccal side of the patient's gum at the work site. The current then flows through the patient and returns to electronic ground via the electrode pads 58, 72 and 82, respectively disposed on the left side of the patient's head, the web of the patient's ipsalateral hand and the web of the patient's contralateral hand. Electrodes 58, 72 and 82 are connected in common to electronic system ground via leads 57, 70 and 80 and respective apparatus terminal ports 52c, 52a and 52b.

In a specific embodiment of the invention, fifty patients with an age distribution of 16-60 years were employed in a study to evaluate the efficiency of the method of the invention using the apparatus described hereinabove. Only healthy (American Society of Anesthesiology (ASA) class I) males and nonpregnant females were considered. There were five categories of dental procedures investigated: periodontics, endodontics, oral surgery, restorative and myofascial pain dysfunction syndrome (MDS). The patients in the last category differed from the others in that they were chronic pain patients. The periodontic procedures performed were prophylaxis with root planing, while the endodontic procedures involved extirpating vital pulp tissue. The oral surgery consisted of extracting erupted third molar teeth. The restorative treatment consisted of removing caries from interproximal, occlusal, or cervical lesions and placing restorations. The myofascial pain dysfunction patients were treated to alleviate muscle spasms and the pain of contraction. The uneven test (30) versus placebo (20) patient numbers were due to patient cancellations during the nine months of the study.

The apparatus used were all identical in appearance and the placebo machines were modified to produce no current even though the dials registered a reading with manipulation of the controls. These machines were numbered for identification purposes by a third party consultant and these numbers were used for computer randomization and patient assignment.

The health history was reviewed and baseline vital signs recorded prior to each patient being brought into the dental operatory.

The protocol design called for a pair of electrodes in the form of a headset being placed, one over each temporal area, to induce transcranial stimulation prior to beginning the dental procedure. These were left in place for ten minutes after the current was adjusted to establish a sub-threshold level. The threshold level was recorded and the operating current reduced to a sub-threshold level.

The secondary electrodes were then placed, the intraoral electrode being inserted in the oral cavity in a buccal position juxtaposed to the operative site. This electrode was contained within a conventional cotton roll. The extraoral electrode was placed on the web of the hand (HO-KU point) between the thumb and index finger of the ipsalateral side of treatment.

Again, an operating threshold was established, a sub-threshold level obtained, and a hand-held control was given to the patient for regulation of the current during the procedure. Patients were informed that increasing the current would produce greater pain control, if required at any time during the procedure.

Patients could terminate the procedure at any time. Vital signs were recorded immediately after the conclusion of the operative event and at 15 and 30 minutes postoperatively.

Of the 50 clinic patients randomly assigned to one of two research groups, 30 (60%) were designated members of the active group and received activated machines. The 20 control (placebo) group patients were given inactivated machines. The design of the study was such that neither patient nor operator had knowledge of whether an active or placebo unit was being employed (double blind). One of the five procedures depicted in Table 1 was performed on each patient. The operation was not related to group (active vs. placebo) assignment. Treatment outcomes were classified as failing or successful based upon patient request for local anesthetic and/or report of pain experienced during the procedure. This straight forward randomized control group comparison conforms to a conventional quasi-experimental design which typically yields findings internally and externally valid.

The result of the study are listed in Table 1. In the active group of thirty patients, twenty-four procedures (80%) were reported as being successful with no need for local anesthesia. Patients reported favorable comments and all stated that this procedure would be their first choice if it was available in future visits. Of the six failures in the test group (20%), three were endodontic procedures, two were oral surgery and one was operative. With the placebo group, fifteen (75%) required local anesthetic. Two cases were completed without a local anesthetic, but the session was rated poor by either patient or operator because of painful stimuli or difficulty in carrying out the procedure. A true placebo effect was experienced with three patients (15%), and all were operative procedures.

Figure 3:
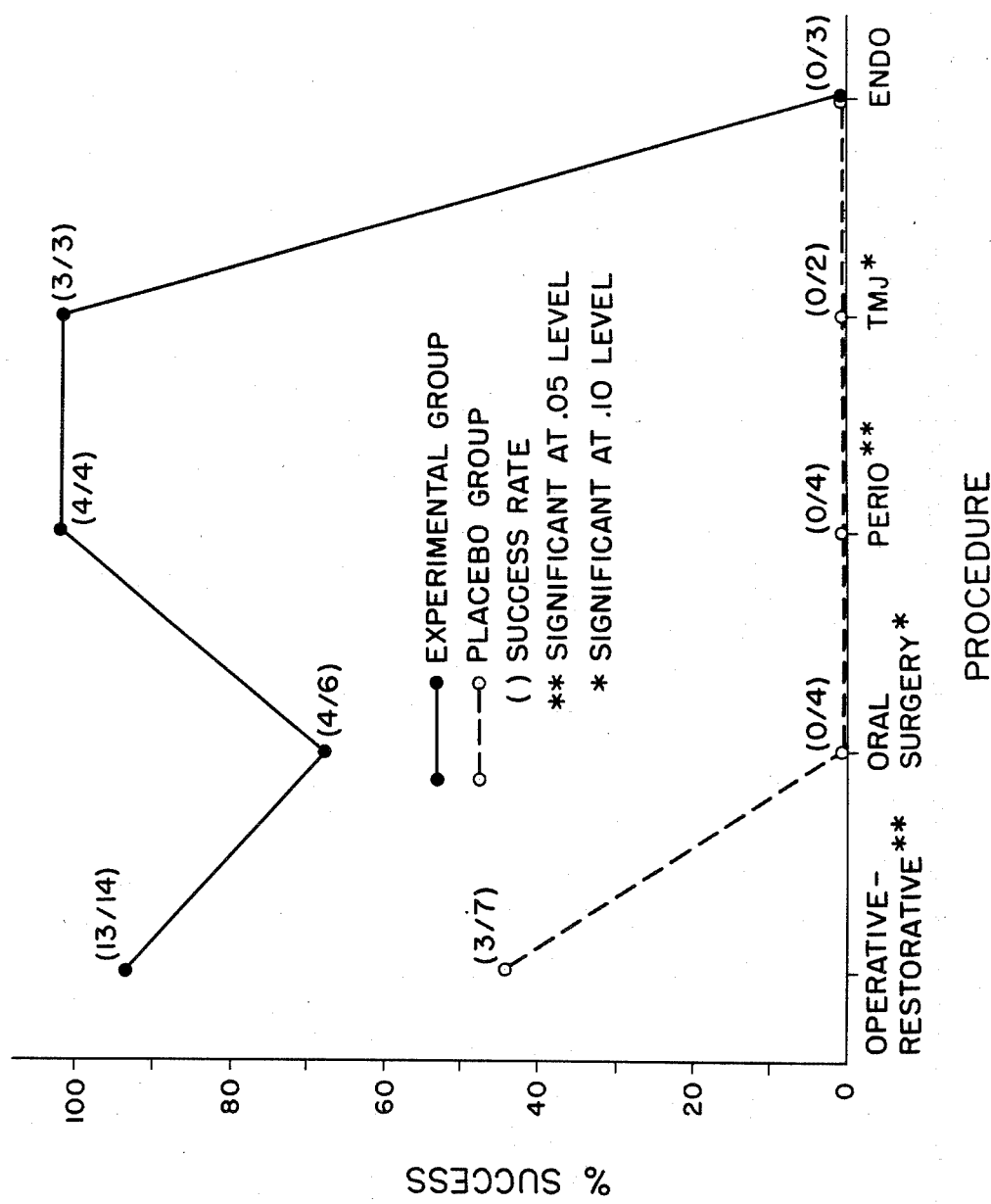
FIG. 3 is a graph showing the percent of success depending upon the specific dental procedure performed.

FIG. 3 demonstrates the successful outcome of the study by procedure. With the operative group, thirteen of fourteen cases were treated successfully in the test group, whereas only three of seven cases were successful in the placebo group. This is significant at the 0.05 level. With respect to oral surgery, four of six cases were successful in the test group compared with no successes with the four patients in the placebo group. This degree of success is significant at the 0.05 level. Similarly, all three patients with temporomandibular joint problems were successfully treated in the test group relative to no successes in the placebo group, a result significant at the 0.10 level. With respect to the endodontic group, the test was not successful for total pain relief, however, for teeth that initially elicited a painful response to palpation or heat or cold, the inventive method did allow penetration of a bur several millimeters into dentin before the patient expressed pain.

TABLE 1

Distribution of subjects; numbers in parentheses tabulate successes.

|  | Active | Placebo | Total |
|---|---|---|---|
| Operative | 14 (13) | 7 (3) | 21 |
| Peridontal | 4 (4) | 4 (0) | 8 |
| MPD | 3 (3) | 3 (0) | 6 |
| Extraction | 6 (4) | 4 (0) | 10 |
| Endodontic | 3 (0) | 2 (0) | 5 |
| Total | 30 (24) | 20 (3) | 50 |

In another embodiment of the invention 600 dental procedures were performed. The inventive method was deemed to be an inadequate means of analgesia if the patient reported 90% or less reduction in pain, or if the patient requested the administration of local anesthetic. Patients excluded from this study were those with a pacemaker, cerebral convulsive disorders, pathologic hypotensive situations, cerebral vascular disorder and pregnancy.

Prior to treatment, a pair of electrodes were placed transcranially with the red (+) contact on the right, anterior to the ear, and the black (−) contact on the left, anterior to the ear. Transcranial stimulation took place for ten minutes. For the prophylactic and root planing procedures, the head set transcranial contact placement was used, as were contacts in the right and left Ho-Ku points. For operative, restorative crowns and surgical procedures, a special electrified cotton roll was connected to the red (+) receptacle of the apparatus. The web of both hand contacts were connected to the black (−) receptacle on the instrument.

Figure 4:
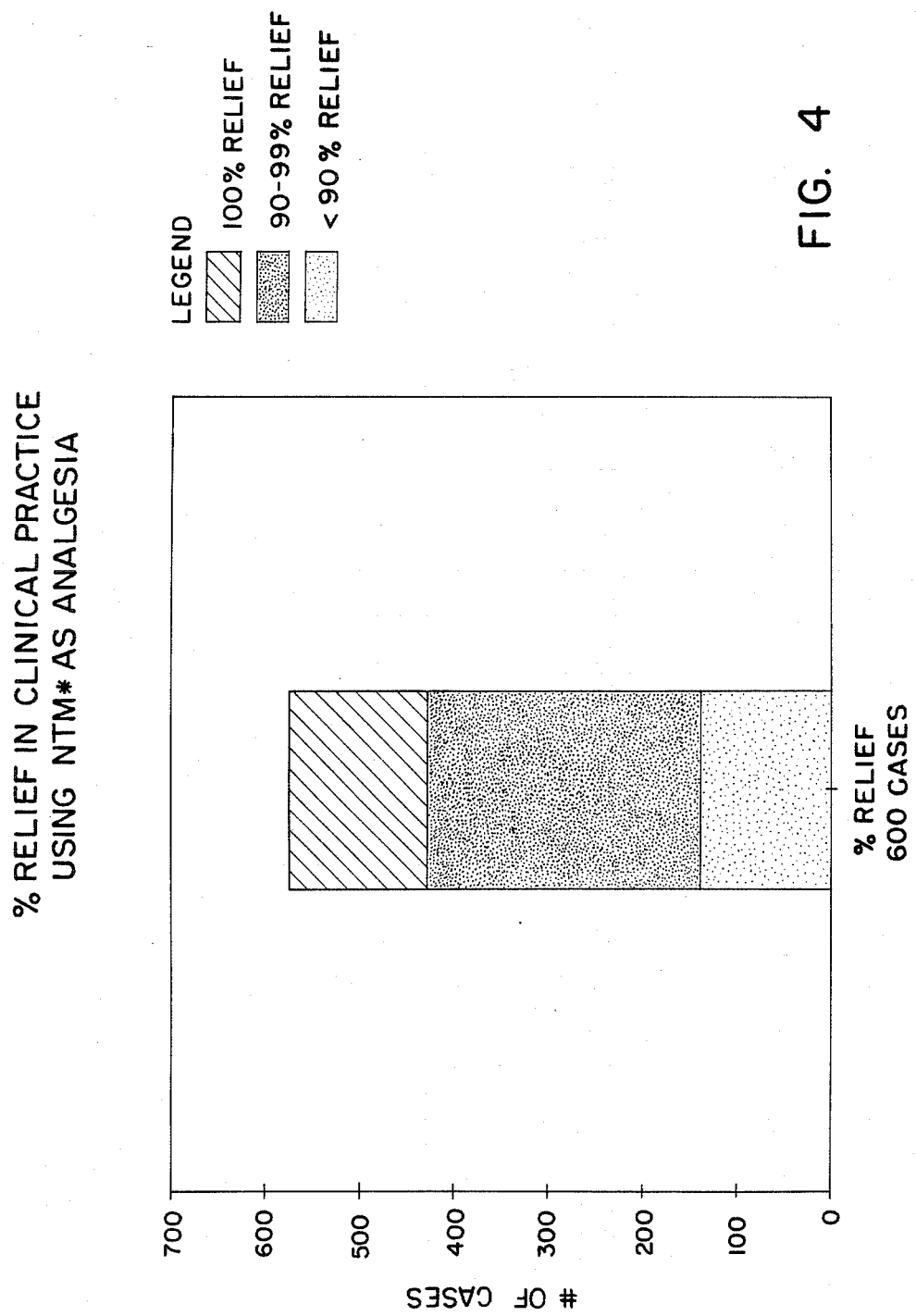
FIG. 4 is a graph showing the percent of relief in clinical practice, using the method of invention.

As shown in FIG. 4, over 76% of the patients in all procedures claimed 90% or better success in the use of the apparatus as dental analgesia.

For scaling and prophylaxis, as shown in FIG. 5, over 83% claimed 90% or better success. For restorative procedures, as shown in FIG. 6, over 76% claimed 90% or better success.

As above noted, the apparatus and methodology of the instant invention, usually per se but sometimes with the administration of supplementary chemical anesthesia, blocks the perception of pain which would otherwise occur by involvement with the fifth cranial or trigeminal nerve system. The apparatus and methodology has manifest advantages for both the dentist and the patient, avoiding the pain, discomfort and delay associated with otherwise required injected chemical anesthesia.

The above described arrangement and methodology are merely illustrative of the principles of the present invention. Numerous modifications and adaptations thereof will be readily apparent to those skilled in the art without departing from the spirit and scope of the present invention.

What is claimed:

1. A method for suppressing pain otherwise associated with a dental procedure in the subject's oral cavity including the steps of securing a first electrode at one side of the head and a second electrode at the opposite side of the head and supplying an electrical wave comprising pulses of high frequency with a low frequency amplitude modulation to said first and said second electrodes.

2. The method of claim 2, in which said first and second electrodes are respectively placed over the right and left temporal areas of the patient's head.

3. The method of claim 1, wherein the frequency of said high frequency electrical wave is in the range of 12-20 khz, wherein said low frequency modulation is in the range 8-20 hz, and wherein said electrical wave does not exceed about 4 milliamperes.

4. The method as in claim 3, wherein said amplitude modulation is non-symmetrical.

5. A method for suppressing pain otherwise associated with a dental procedure in a subject's oral cavity including the steps of securing a first electrode set proximate to the oral cavity of a patient and a second electrode set in an area outside of the oral cavity area, and supplying an electrical wave comprising pulses of high frequency with a low frequency amplitude modulation to said first and said second electrode set.

6. The method of claim 5, wherein the electrode secured proximate to the oral cavity area includes at least one intraoral electrode.

7. The method of claim 5, wherein the frequency of said high frequency electrical wave is in the range 12-20 khz, wherein said low frequency modulation is in the range 8-20 hz, and wherein said electrical wave does not exceed about 4 milliamperes.

8. The method as in claim 7, wherein said amplitude modulation is non-symmetrical.

9. A method for suppressing pain otherwise associated with a dental procedure in a subject's oral cavity including the steps of securing a first electrode at a first side of the head and a second electrode at the buccal side of the gum of a subject adjacent the work area, securing a third electrode to a second side of the head, and supplying an electrical wave comprising pulses of high frequency with a low frequency amplitude modulation to said first, second and third electrodes.

10. The method as in claim 9, wherein the frequency of said high frequency electrical wave is in the range 12-20 khz, wherein said low frequency modulation is in the range 8-20 hz, and wherein said electrical wave does not exceed about 4 milliamperes.

11. The method as in claim 10, wherein said amplitude modulation is non-symmetrical.

12. A method as in claim 9, further comprising the step of securing a further electrode, connected in common to said third electrode, on the web of the subject's ipsalateral hand.

13. A method as in claim 12, wherein the frequency of said high frequency electrical wave is in the range 12-20 khz, wherein said low frequency modulation is in the range 8-20 hz, and wherein said electrical wave does not exceed about 4 milliamperes.

14. A method as in claim 13, wherein said amplitude modulation is non-symmetrical.

15. A method as in claim 9, further comprising the step of securing a further electrode connected in common to said third electrode, on the web of the subject's contralateral hand.

16. A method as in claim 15, wherein the frequency of said high frequency electrical wave is in the range 12-20 khz, wherein said low frequency modulation is in the range 8-20 hz, and wherein said electrical wave does not exceed about 4 milliamperes.

17. A method as in claim 16, wherein said amplitude modulation in non-symmetrical.

18. A method as in claim 12, further comprising the step of securing an additional electrode, connected in common to said third electrode, on the web of the subject's contralateral hand.

19. A method as in claim 18, wherein the frequency of said high frequency electrical wave is in the range 12-20 khz, wherein said low frequency modulation is in the range 8-20 hz, and wherein said electrical wave does not exceed about 4 milliamperes.

20. A method as in claim 19, wherein said amplitude modulation is non-symmetrical.

* * * * *

UNITED STATES PATENT AND TRADEMARK OFFICE
CERTIFICATE OF CORRECTION

PATENT NO. : 4,784,142

DATED : November 15, 1988

INVENTOR(S) : Saul Liss et al.

It is certified that error appears in the above-identified patent and that said Letters Patent is hereby corrected as shown below:

Claim 6, first line of the claim reads "The method of claim 5, wherein the electrode". It should read -- The method of claim 5, wherein the electrode set --.

Claim 2, first line of the claim reads "The method of claim 2, in which said first and". It should read -- The method of claim 1, in which said first and --.

Signed and Sealed this

Sixteenth Day of January, 1990

Attest:

JEFFREY M. SAMUELS

Attesting Officer     Acting Commissioner of Patents and Trademarks